United States Patent
Li et al.

(10) Patent No.: US 11,364,188 B2
(45) Date of Patent: *Jun. 21, 2022

(54) ANTIMICROBIAL PERSONAL CLEANSING COMPOSITIONS

(71) Applicant: Conopco, Inc., Englewood Cliffs, NJ (US)

(72) Inventors: Ningning Li, Bebington (GB); Joseph Muscat, Warrington (GB); Marine Pauline Charlotte Saint-Georges, Garches (FR)

(73) Assignee: Conopco, Inc., Englewood Cliffs, NJ (US)

( * ) Notice: Subject to any disclaimer, the term of this patent is extended or adjusted under 35 U.S.C. 154(b) by 697 days.

This patent is subject to a terminal disclaimer.

(21) Appl. No.: 16/304,932

(22) PCT Filed: May 16, 2017

(86) PCT No.: PCT/EP2017/061756
§ 371 (c)(1),
(2) Date: Nov. 27, 2018

(87) PCT Pub. No.: WO2017/202651
PCT Pub. Date: Nov. 30, 2017

(65) Prior Publication Data
US 2021/0220244 A1     Jul. 22, 2021

(30) Foreign Application Priority Data

May 27, 2016  (EP) ..................... 16171807

(51) Int. Cl.
| | | |
|---|---|---|
| *A61K 8/58* | (2006.01) | |
| *A61K 8/02* | (2006.01) | |
| *A61K 8/20* | (2006.01) | |
| *A61K 8/27* | (2006.01) | |
| *A61K 8/36* | (2006.01) | |
| *A61K 8/46* | (2006.01) | |
| *A61K 8/49* | (2006.01) | |
| *A61K 8/892* | (2006.01) | |
| *A61K 8/92* | (2006.01) | |
| *A61Q 5/02* | (2006.01) | |
| *A61Q 17/00* | (2006.01) | |

(52) U.S. Cl.
CPC .............. *A61K 8/58* (2013.01); *A61K 8/0291* (2013.01); *A61K 8/20* (2013.01); *A61K 8/27* (2013.01); *A61K 8/361* (2013.01); *A61K 8/463* (2013.01); *A61K 8/4933* (2013.01); *A61K 8/892* (2013.01); *A61K 8/92* (2013.01); *A61Q 5/02* (2013.01); *A61Q 17/005* (2013.01); *A61K 2800/49* (2013.01); *A61K 2800/56* (2013.01)

(58) Field of Classification Search
CPC .......... A61K 8/58; A61K 8/0291; A61K 8/20; A61K 8/361; A61K 8/463; A61K 8/892; A61K 8/92; A61K 2800/49; A61K 2800/56; A61K 8/4933; A61K 8/27; A61Q 5/02; A61Q 17/005; A61Q 19/10; A61Q 5/006; A61P 31/10

See application file for complete search history.

(56) References Cited

U.S. PATENT DOCUMENTS

| | | | |
|---|---|---|---|
| 5,348,736 A | 9/1994 | Patel et al. | |
| 7,041,627 B2 * | 5/2006 | Kruse | A61K 8/466 424/70.21 |
| 10,646,414 B2 * | 5/2020 | Bera | A61Q 5/02 |
| 10,888,513 B2 * | 1/2021 | Li | A61K 8/442 |
| 2006/0088557 A1 | 4/2006 | Hassan et al. | |

(Continued)

FOREIGN PATENT DOCUMENTS

| | | |
|---|---|---|
| CN | 1059099 | 3/1992 |
| CN | 101166507 | 4/2008 |

(Continued)

OTHER PUBLICATIONS

Fatima, Marium, et al. "Emulsion separation, classification and stability assessment." RADS Journal of Pharmacy and Pharmaceutical Sciences 2.2 (2014): 56-62. (Year: 2014).*

Ding Tong et al.; Encyclopedia of Chinese Chemical Products; Chemical Industry Press; Oct. 31, 1994; p. 308, with english translation.

Search Report and Written Opinion in PCTEP2017061756; dated Sep. 8, 2017.

Search Report and Written Opinion in EP16171807; dated Oct. 14, 2016.

(Continued)

*Primary Examiner* — Abigail Vanhorn

(74) *Attorney, Agent, or Firm* — Foley & Lardner LLP

(57) ABSTRACT

An antimicrobial personal cleansing composition comprises: (i) an aqueous continuous phase including cleansing surfactant, (ii) a dispersed phase including dispersed particles of zinc-containing antimicrobial agents; and (iii) a solubilised oily liquid conditioning agent for skin and/or hair; which is light mineral oil having a kinematic viscosity of 3 to 5 cS ($mm^2 \cdot s^{-1}$) at 40° C. and is solubilised in wormlike micelles in the aqueous continuous phase via the incorporation of an inorganic electrolyte and a linker molecule of formula $R(X)_n$, wherein R is a $C_6$-$C_{10}$ aryl ring or a $C_3$-$C_{14}$ mono-, di- or trivalent alkyl or hydroxyalkyl chain; n is 1 to 3 and each X is independently selected from —OH, —COOH and —COO$^-$M$^+$ groups, where M is an alkali metal, ammonium or alkanolammonium cation; and in which the level of solubilised oily liquid conditioning agent is 0.45 to 3% by weight based on the total weight of the composition.

12 Claims, No Drawings

(56) References Cited

U.S. PATENT DOCUMENTS

2009/0221463 A1* 9/2009 Kitko ................... A61K 8/86
           510/120
2020/0323764 A1* 10/2020 Li ..................... A61K 8/361

FOREIGN PATENT DOCUMENTS

| JP | 2005511583 | 4/2005 |
| WO | WO03039499 | 5/2003 |
| WO | WO2012084876 | 6/2012 |
| WO | WO2015082241 | 6/2015 |
| WO | WO2016058837 | 4/2016 |

* cited by examiner

ANTIMICROBIAL PERSONAL CLEANSING COMPOSITIONS

CROSS REFERENCE TO RELATED APPLICATIONS

The present application is a U.S. National Phase Application under 35 U.S.C. § 371 of International Application No. PCT/EP2017/061756, filed on May 16, 2017, which claims priority to European patent application No. 16171807.7 filed on May 27, 2016, the contents of which are incorporated herein in their entireties.

FIELD OF THE INVENTION

The present invention relates to antimicrobial personal cleansing compositions such as liquid soaps, body washes and shampoos.

BACKGROUND OF THE INVENTION

In order to provide antimicrobial benefits in a cleansing base such as a liquid soap, body wash or shampoo, it has been proposed to include antimicrobial agents.

WO2016/058837 discloses a hair care composition comprising from 0.1 to 5 wt. % of an anti-dandruff active selected from the group consisting of piroctone olamine, climbazole, selenium sulphide, zinc pyrithione, zinc sulfate and hydrates thereof and mixtures thereof; from 0.01 to 10 wt. % of a mineral oil comprising one or more $C_{15}$-$C_{40}$ hydrocarbons; and, from 1 to 10 wt. % of a fatty acyl isethionate product, which product comprises 40 to 80 wt. % fatty acyl isethionate and 15 to 50 wt. % free fatty acid and/or fatty acid salt.

WO2015/082241 discloses a personal wash composition comprising wormlike micelles comprising 0.1-10% of an oil composition comprising mineral oil and a hydrophilic or lipophilic linker molecule; 6-50% w of a surfactant; 1-25% w of a water soluble electrolyte; and water wherein the linker molecule is selected from saturated mono- or di-carboxylic acid, mono-di- or tri-alcohol, mono hydroxy-di-carboxylic acid, mono hydroxy-tri-carboxylic acid, $C_8$-$C_{22}$ alkyl ethoxy alcohol, $C_1$-$C_3$ alkyl esters of fatty acids, carboxyl amino acid and mixtures thereof; or benzene-dicarboxylic acids, dimethoxybenzene, or mixtures thereof; or mixtures thereof.

WO2015/084876 discloses shampoos and/or hair conditioning agents which contain, in a cosmetic carrier at least one cationic copolymer X which contains the monomers butylacrylate, trimethylammonium ethyl methacrylate chloride and styrene, and at least one active agent positively influencing the metabolic activity on the hair root, selected from biotin; bioquinone; taurine; pantolactone; creatine; theophylline; caffeine; carnitine; an extract from rice, soja, sweetcorn, wheat, colza, algue and/or echinacea; and/or a physiologically compatible salt and/or derivative of said active agents.

Among the preferred types of antimicrobial agent are particulate antimicrobial agents such as zink pyrithione (ZPT). ZPT is active against both gram-positive and gram-negative bacteria, as well as fungi and yeasts. It is widely used in antimicrobial personal cleansing compositions such as anti-dandruff shampoos. Generally, dispersed particles of the ZPT are suspended in the shampoo, which is then applied to the hair to deposit the ZPT particles on the hair and scalp.

Since shampoo is a "rinse-off" product, the level of antimicrobial agent deposited on the hair and scalp can be low. However, incorporation of higher levels of antimicrobial agent is frequently impractical for shampoo for cost reasons. Higher levels of particulate antimicrobial agents (such as ZPT) may also affect product storage stability and impair product visual appeal.

The present invention addresses this problem.

SUMMARY OF THE INVENTION

The invention provides an antimicrobial personal cleansing composition comprising:
(i) an aqueous continuous phase including cleansing surfactant,
(ii) a dispersed phase including dispersed particles of one or more zinc-containing antimicrobial agents; and
(iii) a solubilised oily liquid conditioning agent for skin and/or hair;
in which the oily liquid conditioning agent is light mineral oil having a kinematic viscosity of 3 to 5 cS ($mm^2 \cdot s^{-1}$) at 40° C. and is solubilised in wormlike micelles in the aqueous continuous phase via the incorporation of at least one inorganic electrolyte and at least one linker molecule which is selected from compounds of general formula $R(X)_n$, in which R is an aryl ring having from 6 to 10 carbon atoms or a mono-, di- or trivalent alkyl or hydroxyalkyl chain having from 3 to 14 carbon atoms; n is 1 to 3 and each X is independently selected from —OH, —COOH and —COO$^-$ M$^+$ groups, where M is an alkali metal, ammonium or alkanolammonium cation;
and in which the level of solubilised oily liquid conditioning agent in the conditioning shampoo composition ranges from 0.45 to 3% by weight based on the total weight of the conditioning shampoo composition.

The invention also provides the use of the composition described above for the enhanced deposition of one or more zinc-containing antimicrobial agents onto the skin and/or hair.

DETAILED DESCRIPTION AND PREFERRED EMBODIMENTS

The antimicrobial personal cleansing composition according to the invention comprises an aqueous continuous phase (i) including cleansing surfactant.

As used herein, the term "aqueous continuous phase" is meant a continuous phase which has water as its basis.

Suitably, the composition of the invention will comprise from about 50 to about 90%, preferably from about 55 to about 85%, more preferably from about 60 to about 85%, most preferably from about 65 to about 83% water (by weight based on the total weight of the composition).

The cleansing surfactant may suitably be selected from one or more anionic surfactants. Typical anionic surfactants for use as cleansing surfactants in the invention include those surface active agents which contain an organic hydrophobic group with from 8 to 14 carbon atoms, preferably from 10 to 14 carbon atoms in their molecular structure; and at least one water-solubilizing group which is preferably selected from sulphate, sulphonate, sarcosinate and isethionate.

Specific examples of such anionic surfactants include ammonium lauryl sulphate, ammonium laureth sulphate, trimethylamine lauryl sulphate, trimethylamine laureth sulphate, triethanolamine lauryl sulphate, trimethylethanolamine laureth sulphate, monoethanolamine lauryl sulphate, monoethanolamine laureth sulphate, diethanolamine lauryl sulphate, diethanolamine laureth sulphate, lauric monoglyceride sodium sulphate, sodium lauryl sulphate, sodium laureth sulphate, potassium lauryl sulphate, potassium laureth sulphate, sodium lauryl sarcosinate, sodium lauroyl sarcosinate, lauryl sarcosine, ammonium cocoyl sulphate, ammonium lauroyl sulphate, sodium cocoyl sulphate, sodium lauryl sulphate, potassium cocoyl sulphate, potassium lauryl sulphate, monoethanolamine cocoyl sulphate, monoethanolamine lauryl sulphate, sodium tridecyl benzene sulphonate, sodium dodecyl benzene sulphonate, sodium cocoyl isethionate and mixtures thereof.

A preferred class of anionic surfactants for use as cleansing surfactants in the invention are alkyl ether sulphates of general formula:

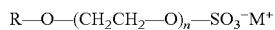

in which R is a straight or branched chain alkyl group having 10 to 14 carbon atoms, n is a number that represents the average degree of ethoxylation and ranges from 1 to 5, preferably from 2 to 3.5, and M is a alkali metal, ammonium or alkanolammonium cation, preferably sodium, potassium, monoethanolammonium or triethanolammonium, or a mixture thereof.

Specific examples of such preferred anionic surfactants include the sodium, potassium, ammonium or ethanolamine salts of $C_{10}$ to $C_{12}$ alkyl sulphates and $C_{10}$ to $C_{12}$ alkyl ether sulphates (for example sodium lauryl ether sulphate), Mixtures of any of the above described materials may also be used.

In a typical composition of the invention the level of cleansing surfactant will generally range from 5 to 26% (by weight based on the total weight of the composition).

The antimicrobial personal cleansing composition according to the invention comprises a solubilised oily liquid conditioning agent (iii) for skin and/or hair.

For the purposes of the present invention, the term "oily liquid" means an oil that is capable of flowing under its own weight under ambient conditions (1 atmosphere, 25° C.). The term "oil" means a non-aqueous compound which is immiscible with water (distilled or equivalent) at a concentration of 0.1 wt %, at 25° C.

Oily liquid conditioning agents (iii) suitable for use in the invention will generally have a kinematic viscosity at 40° C. of 1000 cS ($mm^2 \cdot s^{-1}$) or less, preferably 500 cS ($mm^2 \cdot s^{-1}$) or less, more preferably 50 cS ($mm^2 \cdot s^{-1}$) or less, and most preferably 10 cS ($mm^2 \cdot s^{-1}$) or less, such as from 0.5 to 10 cS ($mm^2 \cdot s^{-1}$).

Suitable oily liquid conditioning agents (iii) for use in the invention may generally be selected from cosmetically acceptable oils such as silicone oils, hydrocarbon-based oils and mixtures thereof.

For the purposes of the present invention, the term "silicone oil" means an oil which contains at least one silicon atom, and more particularly at least one Si—O group. The term "hydrocarbon-based oil" means an oil formed from carbon and hydrogen atoms, and optionally oxygen and nitrogen atoms, and not containing any silicon or fluorine atoms. It may contain alcohol, ester, ether, carboxylic acid, amine and/or amide groups. These oils may be of plant, mineral or synthetic origin.

Examples of suitable silicone oils for use in the invention include linear or cyclic silicone oils having a kinematic viscosity of from about 0.65 to about 50, preferably from about 1.5 to about 5 cS ($mm^2 \cdot s^1$) at 25° C. Example of such materials include linear or cyclic polydimethylsiloxanes having from 2 to 7 siloxane units, such as octamethylcyclotetrasiloxane, decamethylcyclopentasiloxane, dodecamethylcyclohexasiloxane, octamethyltrisiloxane, hexamethyldisiloxane, decamethyltetrasiloxane, dodecamethylpentasiloxane and their mixtures. Preferred are linear polydimethylsiloxanes having from 3 to 5 siloxane units and their mixtures. Such materials are commercially available for example as Dow Corning @ 200 series fluids.

Preferred oily liquid conditioning agents (iii) for use in the invention are generally selected from hydrocarbon-based oils.

Examples of such materials include oily liquid hydrocarbons such as $C_4$-$C_{50}$ straight or branched chain, saturated or unsaturated aliphatic or cycloaliphatic hydrocarbons and mixtures thereof. Straight chain hydrocarbons will preferably contain from about 12 to about 30 carbon atoms. Branched chain hydrocarbons can and typically may contain higher numbers of carbon atoms. Also suitable are polymeric hydrocarbons, such as polymers of $C_{2-6}$ alkenyl monomers (e.g. polyisobutene, polybutene) and poly α-olefin oils derived from 1-alkene monomers having from about 6 to about 16 carbons, preferably from about 6 to about 12 carbon atoms (e.g. polymers derived from 1-octene, 1-decene, 1-dodecene, 1-tetradecene, 1-hexadecene, and mixtures thereof). Polymeric hydrocarbons for use in the invention can be straight or branched chain polymers, and may be hydrogenated. The number average molecular weight of such polymeric materials can vary widely, but will typically range from about 200 up to about 3000.

Preferred oily liquid hydrocarbons for use in the invention include mineral oils. The term "mineral oil" in the context of this invention generally denotes an oily liquid mixture of saturated hydrocarbons with boiling-points greater than 200° C., and which is obtained from petroleum (i.e. a mineral source). Mineral oil saturated hydrocarbons include straight chain (paraffinic), branched chain (isoparaffinic) and cyclic (naphthenic) structures, and molecules containing all three configurations, with the number of carbon atoms per hydrocarbon molecule generally ranging from about $C_{15}$ to about $C_{50}$. Mineral oils suitable for use in the invention are typically obtained from petroleum through various refining steps (e.g. distillation, extraction and/or crystallisation) and subsequent purification (e.g. acid treatment and/or catalytic hydrotreatment).

Mineral oils may also be characterised in terms of their viscosity. "Light" mineral oils will generally have a kinematic viscosity of about 34 cS ($mm^2 \cdot s^{-1}$) or less at 40° C. and "heavy" mineral oils will generally have a kinematic viscosity ranging from about 35 cS ($mm^2 \cdot s^{-1}$) up to about 240 cS ($mm^2 \cdot s^{-1}$) at 40° C.

Light mineral oils (as defined above) are preferred for use in the invention. More preferably such light mineral oils have a kinematic viscosity of about 10 cS ($mm^2 \cdot s^{-1}$) or less at 40° C. Most preferably the kinematic viscosity ranges from about 3 to about 5 cS ($mm^2 \cdot s^{-1}$) at 40° C. Materials of this type are commercially available from Sonneborn Inc. under the brand name Lytol®.

Other suitable hydrocarbon-based oils for use in the invention include oily liquid esters. Oily liquid esters for use in the invention are generally characterised by having at least 10 carbon atoms, and may be either straight-chained or branched. The esters may have hydrocarbyl chains derived from fatty acids or alcohols (e.g. monoesters, polyhydric alcohol esters, and di- and tri-carboxylic acid esters). The hydrocarbyl radicals may include or have covalently bonded thereto other compatible functionalities, such as amides and alkoxy moieties, such as ethoxy or ether linkages.

Examples of oily liquid esters for use in the invention include:

aliphatic monohydric alcohol esters such as $C_5$-$C_{22}$ straight or branched-chain, saturated or unsaturated alkyl esters of $C_1$-$C_{18}$ straight or branched-chain, saturated or unsaturated alkyl alcohols (provided that the total number of carbon atoms in the ester is at least 10), such as isostearyl palmitate, isononyl isononanoate, myristyl propionate, isopropyl isostearate, isopropyl myristate, isopropyl palmitate, ethylhexyl palmitate, cetyl acetate, cetyl propionate, cetyl stearate, isodecyl neopentanoate, cetyl octanoate, isocetyl stearate, ethylhexyl stearate and mixtures thereof;

aliphatic polyhydric alcohol esters such as $C_5$-$C_{22}$ straight or branched-chain, saturated or unsaturated alkyl esters of $C_3$-$C_{30}$ straight or branched-chain, saturated or unsaturated polyols (provided that the total number of carbon atoms in the ester is at least 10), such as propylene glycol dipelargonate, pentaerythrityl tetraoctanoate, trimethylopropane tricaprylate/tricaprate, trioctanoin, pentaerythrityl tetrapelargonate, sorbitan trioleate, caprylic/capric triglyceride, neopentyl alcohol tetraoctanoate, and mixtures thereof;

aliphatic polycarboxylic acid polyesters such as $C_5$-$C_{22}$ straight or branched-chain, saturated or unsaturated alkyl diesters of $C_2$-$C_{10}$ straight or branched-chain, saturated or unsaturated dicarboxylic acids (provided that the total number of carbon atoms in the ester is at least 10), such as diisopropyl adipate, dioctyl sebacate, dioctyl succinate, dioctyl maleate, diisostearyl adipate, diethyl sebacate, diisostearyl fumarate, dioctyl adipate and mixtures thereof; and/or $C_5$-$C_{22}$ straight or branched-chain, saturated or unsaturated alkyl triesters of $C_6$-$C_{10}$ straight or branched-chain, saturated or unsaturated tricarboxylic acids (provided that the total number of carbon atoms in the ester is at least 10), such as trioctyldodecyl citrate, triisostearyl citrate, triisopropyl citrate and mixtures thereof; and aliphatic esters of aromatic acids such as $C_{12}$-$C_{15}$ branched or unsaturated alkyl esters of benzoic acid.

Preferred oily liquid esters for use in the invention may be selected from the aliphatic monohydric and/or polyhydric alcohol esters which are described in more detail above.

Mixtures of any of the above-described materials may also be used.

The level of oily liquid conditioning agent (iii) in compositions of the invention depends on the particular material (s) used, but generally ranges from about 0.5 to about 3% by weight based on the total weight of the composition.

In a preferred composition according to the invention the oily liquid conditioning agent (iii) is selected from oily liquid hydrocarbons, oily liquid esters and mixtures thereof, at a level ranging from about 0.45 to about 2%, more preferably from about 0.5 to about 1.5% (by weight based on the total weight of the composition).

In a particularly preferred composition according to the invention the oily liquid conditioning agent (iii) is light mineral oil (as defined above), at a level ranging from about 0.5 to about 1.5% (by weight based on the total weight of the composition).

In the composition according to the invention, the oily liquid conditioning agent (iii) is solubilised in wormlike micelles in the aqueous continuous phase (i). Typically the solubilised oily liquid conditioning agent (iii) forms a microemulsion which is stable to phase separation.

"Wormlike micelles" in the context of this invention are elongated and flexible aggregates formed by the self-assembly of surfactant molecules in water. Above a threshold concentration, wormlike micelles entangle into a transient network, reminiscent of polymer solutions, and display viscoelastic properties. However, unlike a covalently bonded polymer backbone, the micelles are in a state of thermodynamic equilibrium with the solvent and are perpetually broken and reformed under Brownian fluctuations. This leads to a broad and dynamic distribution of micelle lengths which can change under an imposed shear or extensional flow.

Wormlike micelles can be fully described by a number of structural parameters, which cover a broad range of length-scales. The overall length of the micelles is referred to as the contour length L and varies between a few (e.g. about 1 to 10) nanometers up to a few (e.g. about 1 or 2) microns. Cryo-TEM provides a direct visualization of the micelles and can be used to estimate the contour length, while light and neutron scattering give a more accurate determination. Radii of wormlike micelles are typically a few (e.g. about 1 to 10) nm. Another key structural parameter in the description of wormlike micelles is the persistence length $l_p$, the length over which the micelles are considered rigid. Although wormlike micelles can be extremely flexible and micrometres long, their large cross-section implies that on smaller length-scales (of order $l_p$) they act as rigid rods. Techniques such as rheology, light and neutron scattering and flow birefringence have been employed to estimate $l_p$, as well as simulations. Experimentally, persistence lengths from about 10 to about 40 nm have been reported in neutral systems. For charged wormlike micelles, the persistence length varies significantly with surfactant structure, counter-ion and salt concentration, but is typically a few tens of nanometers (e.g about 30 to about 100 nm).

The oily liquid conditioning agent (iii) is solubilised in wormlike micelles in the aqueous continuous phase via the incorporation of at least one inorganic electrolyte and at least one linker molecule of general formula $R(X)_n$ as defined above.

"Linker molecules" in the context of this invention are chemical additives used in surfactant systems that enhance the surfactant-oil or surfactant-water interactions. Lipophilic linkers segregate near the oil side of the interface close to the tails of the surfactants. The presence of the lipophilic linker extends the impact of the surfactant deeper into the oil phase and may promote additional orientation of the oil molecules. Hydrophilic linkers are surfactant-like molecules that coadsorb with the surfactant at the oil/water interface, but have a minimal interaction with the oil molecules. The adsorption of the hydrophilic linker at the oil/water interface increases the total interfacial area.

R in the general formula $R(X)_n$ above is preferably a phenyl ring or a mono-, di- or trivalent linear alkyl or hydroxyalkyl chain having from 3 to 12 carbon atoms.

Preferred linker molecules for use in the invention include:

aromatic carboxylic acids of formula $R(X)_n$ as defined above, in which R is a phenyl ring; n is 1 or 2 and each X is independently selected from —COOH and —COO$^-$M$^+$ groups, where M is as defined above, preferably sodium or potassium;

linear aliphatic mono-, di- or tricarboxylic acids of formula $R(X)_n$ as defined above, in which R is a mono-, di- or trivalent, linear, alkyl or hydroxyalkyl chain having from 3 to 12, preferably from 6 to 10 carbon atoms, and each X is independently selected from —COOH and —COO$^-$M$^+$ groups, where M is as defined above, preferably sodium or potassium, and linear aliphatic diols of formula $R(X)_n$ as defined above, in which R is a divalent linear alkyl chain having from 3 to 12 carbon atoms.

Examples of preferred linker molecules for use in the invention include benzoic acid, citric acid, phthalic acid, caprylic acid, lauric acid, azelaic acid (and/or their sodium or potassium salts) and 1,12-dodecanediol.

Mixtures of any of the above described materials may also be suitable.

The level of linker molecule (as defined above) in compositions of the invention preferably ranges from about 0.01 to about 1%, more preferably from about 0.02 to about 0.5%, most preferably from about 0.05 to about 0.15% by weight based on the total weight of the composition.

The weight ratio of solubilised oily liquid conditioning agent (iii) to linker molecule (as defined above) in compositions of the invention generally ranges from about 15:1 to about 1:1, preferably from about 12:1 to about 6:1, more preferably from about 10:1 to about 8:1. A particularly preferred composition according to the invention comprises caprylic acid as the linker molecule, in combination with light mineral oil as the solubilised oily liquid conditioning agent (iii), in the amounts and ratios given above.

The composition according to the invention includes at least one inorganic electrolyte. The inorganic electrolyte is used to assist in the solubilisation of the oily liquid conditioning agent (iii) and to provide viscosity to the composition.

The viscosity of the composition of the invention suitably ranges from 3,000 to 10,000 mPa·s, preferably from 4,000 to 9,000 mPa·s when measured using a Brookfield V2 viscometer (spindle RTV5, 1 minute, 20 rpm) at 30° C.

Suitable inorganic electrolytes include metal chlorides (such as sodium chloride, potassium chloride, calcium chloride, magnesium chloride, zinc chloride, ferric chloride and aluminium chloride) and metal sulphates (such as sodium sulphate and magnesium sulphate).

Examples of preferred inorganic electrolytes for use in the invention include sodium chloride, potassium chloride, magnesium sulphate and mixtures thereof.

Mixtures of any of the above described materials may also be suitable.

The level of inorganic electrolyte in compositions of the invention depends on the particular oily liquid conditioning agent (iii) used, but generally ranges from about 1 to about 25%, preferably from about 1.5 to about 20% (by total weight inorganic electrolyte based on the total weight of the composition).

A particularly preferred composition according to the invention comprises sodium chloride as the inorganic electrolyte, in the amounts given above.

The composition of the invention comprises a dispersed phase (ii) including dispersed particles of one or more zinc-containing antimicrobial agents.

A preferred example of a zinc-containing antimicrobial agent for use in the invention is zinc pyrithione (ZPT).

Zinc pyrithione (ZPT) has the following chemical structure:

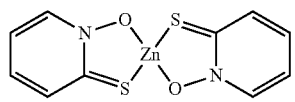

The zinc pyrithione particles may be amorphous, or may take various regular or irregular crystalline forms such as rods, needles, blocks, platelets and mixtures thereof. The average particle diameter of the zinc pyrithione particles (maximum dimension) is typically from about 0.1 to about 50 µm, preferably from about 0.1 m to about 10 µm, more preferably from about 0.1 µm to about 5 µm as determined, for example, using a Horiba LA-910 Laser scattering particle size distribution analyzer.

Other zinc-containing antimicrobial agents which may be used in the invention include zinc salts of organic acids, zinc salts of inorganic acids, zinc oxides, zinc hydroxides and mixtures thereof.

Preferred examples of such materials include zinc oxide, zinc citrate, zinc malonate, zinc carbonate and mixtures thereof.

Mixtures of any of the above described materials may also be suitable.

The level of zinc-containing antimicrobial agent(s) in compositions of the invention depends on the particular material (s) used, but generally ranges from about 0.1 to about 5% by total weight zinc-containing antimicrobial agent(s) based on the total weight of the composition.

In a particularly preferred composition according to the invention the zinc-containing antimicrobial agent is zinc pyrithione, at a level ranging from about 0.2 to about about 3%, more preferably from about 0.25 to about 2.5% by weight based on the total weight of the composition.

The composition of the invention may also include additional antimicrobial agents such as octopirox (piroctone olamine), azole antimicrobials (e.g. climbazole, ketoconazole), selenium sulfide and mixtures thereof. When included, amounts of these materials may range from about 0.01 to about 5%, preferably from 0.1 to 3%, and optimally from about 0.3 to about 4% by weight based on the total weight of the composition.

The dispersed phase (ii) of the composition of the invention may also include emulsified droplets of non-volatile silicone having a mean droplet diameter (D3,2) of 1 micrometre or less. Preferably the mean droplet diameter (D3,2) is 1 micrometre or less, more preferably 0.5 micrometre or less, and most preferably 0.25 micrometre or less.

A suitable method for measuring the mean droplet diameter (D3,2) is by laser light scattering using an instrument such as a Malvern Mastersizer.

The term "non-volatile silicone" in the context of this invention means a silicone with a vapour pressure of less than 1000 Pa at 25° C.

Suitable silicones for use in the invention include polydiorganosiloxanes, in particular polydimethylsiloxanes (dimethicones), polydimethyl siloxanes having hydroxyl end groups (dimethiconols), and amino-functional polydimethylsiloxanes (amodimethicones).

Suitable silicones preferably have a molecular weight of greater than 100,000 and more preferably a molecular weight of greater than 250,000.

All molecular weights as used herein are weight average molecular weights, unless otherwise specified.

Suitable silicones preferably have a kinematic viscosity of greater than 50,000 cS (mm$^2$·s$^{-1}$) and more preferably a kinematic viscosity of greater than 500,000 cS (mm$^2$·s$^{-1}$). Silicone kinematic viscosities in the context of this invention are measured at 25° C. and can be measured by means of a glass capillary viscometer as set out further in Dow Corning Corporate Test Method CTM004 Jul. 20, 1970.

Suitable silicones for use in the invention are available as pre-formed silicone emulsions from suppliers such as Dow Corning and GE Silicones. The use of such pre-formed silicone emulsions is preferred for ease of processing and control of silicone particle size. Such pre-formed silicone emulsions will typically additionally comprise a suitable emulsifier, and may be prepared by a chemical emulsification process such as emulsion polymerisation, or by mechanical emulsification using a high shear mixer. Pre-formed silicone emulsions having a mean droplet diameter (D3,2) of less than 0.15 micrometers are generally termed microemulsions.

Examples of suitable pre-formed silicone emulsions include emulsions DC2-1766, DC2-1784, DC-1785, DC-1786, DC-1788, DC-1310, DC-7123 and microemulsions DC2-1865 and DC2-1870, all available from Dow Corning. These are all emulsions/microemulsions of dimethiconol. Also suitable are amodimethicone emulsions such as DC939 (from Dow Corning) and SME253 (from GE Silicones).

Mixtures of any of the above described silicone emulsions may also be used.

When included, the amount of emulsified, non-volatile silicone in compositions of the invention may suitably range from 0.05 to 10%, preferably from 0.2 to 8% (by total weight silicone based on the total weight of the composition).

The composition of the invention preferably includes one or more cationic polymers. Such polymers may enhance the delivery of conditioning agents and thereby improve the conditioning benefits obtained.

Cationic polymers typically contain cationic nitrogen-containing groups such as quaternary ammonium or protonated amino groups. The cationic protonated amines can be primary, secondary, or tertiary amines (preferably secondary or tertiary). The average molecular weight of the cationic polymer is preferably from 5,000 to 10 million. The cationic polymer preferably has a cationic charge density of from 0.2 meq/gm to 7 meq/gm.

The term "cationic charge density" in the context of this invention refers to the ratio of the number of positive charges on a monomeric unit of which a polymer is comprised to the molecular weight of the monomeric unit. The charge density multiplied by the polymer molecular weight determines the number of positively charged sites on a given polymer chain.

The cationic nitrogen-containing moiety of the cationic polymer is generally present as a substituent on all, or more typically on some, of the repeat units thereof. The cationic polymer may be a homo-polymer or co-polymer of quaternary ammonium or cationic amine-substituted repeat units, optionally in combination with non-cationic repeat units. Particularly suitable cationic polymers for use in the invention include cationic polysaccharide polymers, such as cationic cellulose derivatives, cationic starch derivatives, and cationic guar gum derivatives.

A particularly suitable type of cationic polysaccharide polymer that can be used is a cationic guar gum derivative, such as guar hydroxypropyltrimethylammonium chloride. (commercially available from Rhodia® in their JAGUAR® trademark series). Examples of such materials are JAGUAR® C13S, JAGUAR® C14, JAGUAR® C15 and JAGUAR® C17.

Mixtures of any of the above described cationic polymers may also be used.

When included, the total level of cationic polymer in the composition of the invention is preferably from 0.05% to 2% and more preferably from 0.1 to 0.5% by weight based on the total weight of the composition.

The composition of the invention preferably includes one or more amphoteric surfactants.

Suitable amphoteric surfactants are betaines, such as those having the general formula $R(CH_3)_2N^+CH_2COO^-$, where R is an alkyl or alkylamidoalkyl group, the alkyl group preferably having 10 to 16 carbon atoms. Particularly suitable betaines are oleyl betaine, caprylamidopropyl betaine, lauramidopropyl betaine, isostearylamidopropyl betaine, and cocoamidopropyl betaine.

When included, the total level of amphoteric surfactant is generally from 0.1% to 20%, preferably from 1% to 10%, more preferably from 1% to 5% by weight based on the total weight of the composition.

The composition of the invention preferably includes one or more suspending agents. Suitable suspending agents include polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives.

Mixtures of any of the above suspending agents may be used. Preferred is a mixture of cross-linked polymer of acrylic acid and crystalline long chain acyl derivative.

When included, the total level of suspending agent is generally 0.1 to 10%, preferably from 0.5 to 6%, more preferably from 0.9 to 4% by weight based on the total weight of the composition.

The pH of the composition preferably ranges from 4 to 7, more preferably from 5 to 7.

A composition according to the invention may contain further optional ingredients to enhance performance and/or consumer acceptability. Examples of such ingredients include fragrance, dyes and pigments, pH adjusting agents and preservatives or antimicrobials. Each of these ingredients will be present in an amount effective to accomplish its purpose. Generally these optional ingredients are included individually at a level of up to 5% by weight based on the total weight of the composition.

Typically the composition of the invention is topically applied to the hair and then massaged into the hair and scalp. The composition is then rinsed off the hair and scalp with water prior to drying the hair.

The invention will be further illustrated by the following, non-limiting Examples, in which all percentages quoted are by weight based on total weight unless otherwise stated.

EXAMPLES

Hair cleansing shampoo formulations were prepared, having ingredients as shown in Table 1. Examples 1 to 4 represent formulations according to the invention.

TABLE 1

| Ingredient | Control (% w/w) | Example 1 (% w/w) | Example 2 (% w/w) | Example 3 (% w/w) | Example 4 (% w/w) |
|---|---|---|---|---|---|
| Sodium laureth sulphate (1EO) | 11.6 | 11.6 | 11.6 | 11.6 | 11.6 |
| Cocamidopropyl betaine | 1.5 | 1.5 | 1.5 | 1.5 | 1.5 |

TABLE 1-continued

| Ingredient | Control (% w/w) | Example 1 (% w/w) | Example 2 (% w/w) | Example 3 (% w/w) | Example 4 (% w/w) |
|---|---|---|---|---|---|
| Guar hydroxypropyltrimonium chloride | 0.2 | 0.2 | 0.2 | 0.2 | 0.2 |
| Dimethiconol* | 1 | 1 | 1 | 1 | 1 |
| Carbomer | 0.4 | 0.4 | 0.4 | 0.4 | 0.4 |
| Ethylene glycol distearate | 0.6 | 0.6 | 0.6 | 0.6 | 0.6 |
| Mica | 0.2 | 0.2 | 0.2 | 0.2 | 0.2 |
| Disodium EDTA | 0.1 | 0.1 | 0.1 | 0.1 | 0.1 |
| Zinc pyrithione | 1 | 1 | 1 | 1 | 1 |
| Sodium hydroxide | 0.2 | 0.2 | 0.3 | 0.3 | 0.3 |
| Sodium chloride | 0.5 | 2 | 3 | 3.6 | 4.2 |
| Caprylic acid | 0 | 0.05 | 0.1 | 0.15 | 0.2 |
| Lytol ® mineral oil | 0 | 0.45 | 0.9 | 1.35 | 1.8 |
| Water, perfume, preservatives | to 100% | to 100% | to 100% | to 100% | to 100% |

*Emulsion of dimethiconol with anionic emulsifier, average particle size < 1 micron (ex Dow Corning)

Measurement of Zinc Deposition

The formulations described in Table 1 were assessed for their zinc deposition onto virgin (untreated) hair using the following protocol:

0.25 g test formulation is applied to a wet 2.5 g/6" switch of virgin dark brown European (DBE) hair. The test formulation is massaged on the switch for 30 seconds followed by rinsing with warm water for 30 seconds. This treatment is repeated twice. Zinc deposition is measured by X-ray Fluorescence (XRF). Five replicas were produced for each test formulation. The average of measured zinc deposition is shown in Table 2.

TABLE 2

| | Test formulation | | | | |
|---|---|---|---|---|---|
| | Control | Example 1 | Example 2 | Example 3 | Example 4 |
| Mean deposition/ppm | 418 | 775 | 709 | 899 | 811 |
| Standard deviation | 93 | 95 | 114 | 53 | 150 |

The results show that Examples 1 to 4 (according to the invention) deposit significantly more zinc than the control (not according to the invention). This improved zinc deposition was confirmed as statistically significant by both P value and t-test.

The formulations described in Table 1 were also assessed for their zinc deposition onto damaged hair using the same test protocol as described above, but instead using wet 2.5 g/6" switches of double bleached European hair. Again, five replicas were produced for each test formulation. The average of measured zinc deposition is shown in Table 3.

TABLE 3

| | Test formulation | | | | |
|---|---|---|---|---|---|
| | Control | Example 1 | Example 2 | Example 3 | Example 4 |
| Mean deposition/ppm | 413 | 650 | 576 | 646 | 599 |
| Standard deviation | 71 | 108 | 124 | 89 | 176 |

Again the results show that Examples 1 to 4 (according to the invention) deposit significantly more zinc than the control (not according to the invention). This improved zinc deposition was confirmed as statistically significant by both P value and t-test.

The invention claimed is:

1. An antimicrobial personal cleansing composition comprising:
   (i) an aqueous continuous phase comprising a cleansing surfactant,
   (ii) a dispersed phase consisting of dispersed particles of one or more zinc containing antimicrobial agents; and
   (iii) a solubilized oily liquid conditioning agent for skin and/or hair;
   wherein:
   the solubilized oily liquid conditioning agent is light mineral oil having a kinematic viscosity of 3 to 5 cS ($mm^2 \cdot s^{-1}$) at 40° C. and is solubilized in wormlike micelles in the aqueous continuous phase via the incorporation of at least one inorganic electrolyte and at least one linker molecule,
   wherein the at least one linker molecule is selected from compounds of general formula $R(X)_n—$, wherein R is an aryl ring having from 6 to 10 carbon atoms or a mono-, di- or trivalent alkyl or hydroxyalkyl chain having from 3 to 14 carbon atoms; n is 1 to 3 and each X is independently selected from OH, —COOH and —COO-M+ groups, where M+ is an alkali metal, ammonium or alkanolammonium cation; and
   the level of solubilized oily liquid conditioning agent in the antimicrobial personal care composition ranges from 0.45 to 3% by weight based on the total weight of the antimicrobial personal care composition.

2. The antimicrobial personal care composition according to claim 1, wherein the one or more zinc-containing antimicrobial agent is zinc pyrithione, and the antimicrobial agent is present at a level ranging from 0.25 to 2.5% by weight based on the total weight of the antimicrobial personal care composition.

3. The antimicrobial personal care composition according to claim 1, wherein the level of the light mineral oil ranges from 0.5 to 1.5% by weight based on the total weight of the antimicrobial personal care composition.

4. The antimicrobial personal care composition according to claim 1, wherein R is a phenyl ring or a mono-, di- or trivalent linear alkyl or hydroxyalkyl chain having from 3 to 12 carbon atoms.

5. The antimicrobial personal care composition according to claim 4, wherein the at least one linker molecule is caprylic acid.

6. The antimicrobial personal care composition according to claim 1, wherein the level of the at least one linker molecule ranges from 0.05 to 0.15% by weight based on the total weight of the antimicrobial personal care composition.

7. The antimicrobial personal care composition of claim 1, wherein the solubilized oily liquid conditioning agent and at least one linker molecule are present in the antimicrobial personal care composition at a weight ratio from about 15:1 to about 1:1.

8. The antimicrobial personal care composition of claim 1, wherein the at least one inorganic electrolyte is a metal chloride or metal sulphate selected from sodium chloride, potassium chloride, calcium chloride, magnesium chloride, zinc chloride, ferric chloride, aluminium chloride, sodium sulphate, magnesium sulphate, or mixtures thereof.

9. The antimicrobial personal care composition of claim 1, wherein the composition further comprises a non-volatile silicone selected from the group consisting of polydimethylsiloxanes, polydimethyl siloxanes having hydroxyl end groups, amino-functional polydimethylsiloxanes, or a mixture thereof.

10. The antimicrobial personal care composition of claim 1, wherein the cleansing surfactant is selected from one or more anionic surfactants.

11. The antimicrobial personal care composition of claim 1, wherein the cleansing surfactant is present at a level from 5% to 26% by weight based on the total weight of the antimicrobial personal care composition.

12. A method of treating skin and/or hair, the method comprising the steps of:
   applying the antimicrobial personal cleansing composition according to claim 1 to the skin and/or hair; and
   rinsing off the skin and/or hair to remove the antimicrobial personal cleansing composition;
   wherein the method causes deposition of one or more zinc-containing antimicrobial agents onto the skin and/or hair.

* * * * *